United States Patent [19]
Colliopoulos

[11] Patent Number: 5,232,699
[45] Date of Patent: Aug. 3, 1993

[54] LAXATIVE COMPOSITIONS

[75] Inventor: John A. Colliopoulos, Cincinnati, Ohio

[73] Assignee: The Proctor & Gamble Company, Cincinnati, Ohio

[21] Appl. No.: 902,479

[22] Filed: Jun. 19, 1992

Related U.S. Application Data

[63] Continuation of Ser. No. 807,762, Dec. 6, 1991, abandoned, which is a continuation of Ser. No. 558,547, Jul. 26, 1990, abandoned.

[51] Int. Cl.$^5$ ...................... A61K 35/78; A61K 31/20
[52] U.S. Cl. .................................. 424/195.1; 514/558; 514/892
[58] Field of Search ...................... 424/195.1; 514/558, 514/892

[56] References Cited

U.S. PATENT DOCUMENTS

| | | | |
|---|---|---|---|
| 4,256,875 | 3/1981 | Gabriel et al. ........................... 536/4 |
| 4,402,944 | 9/1983 | Callahan et al. ..................... 424/180 |
| 4,476,121 | 10/1984 | Moss ................................... 424/195 |
| 4,511,561 | 4/1985 | Madaus et al. ................... 424/195.1 |
| 4,595,592 | 6/1986 | Hietala ............................. 424/195.1 |
| 4,766,004 | 8/1988 | Moskowitz ........................... 426/658 |
| 4,842,865 | 6/1989 | Durr et al. ........................... 424/456 |
| 4,857,331 | 8/1989 | Shaw et al. ........................... 424/440 |

OTHER PUBLICATIONS

Perdiem ® (sold by Rorer Consumer Pharmaceuticals), *Physicians' Desk Reference for Nonprescription Drugs*, 10th Edition (Medical Economics Company Inc.; 1989) pp. 666–667.

Ex-Lax ® Chocolated Laxative (sold by Sandoz Consumer), *Physicians' Desk Reference for Nonprescription Drugs*, 10th Edition (Medical Economics Company Inc.; 1989), p. 677.

*Primary Examiner*—John W. Rollins
*Attorney, Agent, or Firm*—Kim William Zerby; Douglas C. Mohl; Richard C. Witte

[57] ABSTRACT

The present invention relates to laxative compositions comprising psyllium and sennoside wherein sennoside is dispersed in a palatable food grade fat having a melting point within the range of from about 30° C. to about 50° C.

3 Claims, No Drawings

LAXATIVE COMPOSITIONS

This is a continuation of application Ser. No. 07/807,762, filed Dec. 6, 1991, now abandoned, which is a continuation of application Ser. No. 558,547, filed Jul. 26, 1990, now abandoned.

BACKGROUND OF THE INVENTION

The present invention relates to laxative compositions containing sennosides and psyllium, wherein sennoside is dispersed in a palatable food grade fat having a melting point within the range of from about 30° C. to about 50° C., and to methods for treating constipation by ingesting compositions of the present invention.

The use of senna, sennosides, and psyllium as natural laxatives is known. In fact, a senna/psyllium product is commercially available in dry granule form (Perdiem ®, sold by Rorer). Negative aesthetics and performance attributes are recognized with using senna-containing laxative compositions. Madaus et al. U.S. Pat. No. 4,511,561, issued Apr. 16, 1985, reports that undesirable side effects such as convulsions and pain production may be observed with the use of sennosides. This U.S. Patent describes certain compositions containing psyllium and senna resulting from a specific granulation procedure.

U.S. Pat. No. 4,857,331, issued Aug. 15, 1989, to Shaw et al., teaches ingestible gels confectionary delivery system which is said to include a pectin gel component, an algin gel component and a polymer network gel component, as well as an active ingredient. It is stated therein that sennosides are known to taste unpleasant.

U.S. Patent 4,766,004, issued Aug. 23, 1988 to Moskowitz, describes dietary fiber supplement compositions said to be crunchy and highly palatable containing whole psyllium husk having particle size of 12 to 70 mesh. Also required is palatable food grade vegetable fat which is solid at room temperature, a sweetening agent, and at least one flavoring agent.

U.S. Patents relating to senna-containing compositions include: U.S. Pat. No. 4,842,865, issued Jun. 27, 1989 to Durr et al. (relates to the use of glycofurol for liquidization of pharmaceutical preparations containing more than 50% phosphatidyl choline with a high content of unsaturated fatty acid, which preparations can contain another active ingredient, one of which is stated to be senna extract); U.S. Pat. No. 4,595,592, issued Jun. 17, 1986 to Hietala (relates to a process for obtaining laxative compounds from senna drug by extraction of senna drug); U.S. Pat. No. 4,476,121, issued Oct. 9, 1984 to Moss (relates to orally administered compositions useful for treating constipation comprising a synergistic mixture of fruits, glycerine and compound senna); U.S. Pat. No. 4,402,944, issued Sep. 6, 1983 to Callahan et al. (relates to polysulfonated sennoside A and B derivatives; Example 10 describes an injectable oil comprising the active compound and sesame oil); and U.S. Pat. No. 4,256,875, issued Mar. 27, 1981 to Gabriel et al. (relates to a process for extraction of sennoside from senna).

In spite of the work performed to develop laxative products, there continues to be a need for new compositions which have improved aesthetics and/or reduced undesirable side effects and/or improved consumer acceptability to encourage regular compliance for treating constipation, which are in convenient dosage forms, and which are effective as laxatives.

An object of the present invention is therefore to provide psyllium/sennoside-containing compositions which have improved aesthetics and/or reduced undesirable side effects to encourage easier consumer compliance with regular therapeutic use to treat constipation. A further object is to provide convenient dosage forms (especially in unit dosage form comprising psyllium in a baked composition) containing sennosides and psyllium which are effective for treating constipation. An object is also to provide methods for manufacturing sennoside/psyllium-containing compositions whereby the efficacy and stability of the sennosides and the psyllium is maintained, the sennosides are easily processed, and the resulting product is highly palatable and has the sennoside uniformly available by each product. A further object is to provide methods for treating constipation in humans and lower animals by orally administering psyllium/sennoside-containing compositions according to the present invention.

These and other objects of the present invention will become readily apparent from the detailed description which follows.

All percentages and ratios used herein are by weight unless otherwise specified.

SUMMARY OF THE INVENTION

This invention relates to laxative compositions comprising a safe and effective amount of sennoside, a safe and effective amount of psyllium, and from about 1% to about 50% of a palatable food grade fat having a melting point within the range of from about 30° C. to about 50° C., and wherein further the sennoside is dispersed (in whole or in part) in said fat. Furthermore, it is preferred that such compositions contain a sennoside/fat-containing phase and a psyllium-containing phase.

The present invention further relates to methods for treating constipation in humans or lower animals. These methods comprise orally administering to a human or lower animal in need of such treatment a safe and effective amount of a composition according to the present invention.

Also, the present invention relates to methods for manufacturing psyllium/sennoside-containing compositions. Said methods comprise the steps of: (a) heating to melt a palatable food grade fat having a melting point within the range of from about 30° C. to about 50° C.; (b) mixing sennosides with said melted fat at a temperature not above about 75° C.; and (c) combining the sennoside/fat-containing mixture with psyllium (preferably by coating a psyllium-containing composition).

DETAILED DESCRIPTION OF THE INVENTION

The present invention relates to psyllium/sennoside-containing laxative compositions. These compositions comprise: (a) psyllium fiber; (b) sennosides; and (c) palatable food grade fat having a melting point within the range of from about 30° C. to about 50° C. The sennoside is dispersed in the food grade fat. Optional components suitable for ingestion include: other dietary fiber (especially insoluble dietary fiber); shortening; flour; sweetening agent; and flavoring agent. The components for use in laxative compositions of the present invention, and the amounts preferred to be utilized, are described in detail hereinafter.

(a) Psyllium Fiber

The present laxative compositions comprise psyllium fiber. The term "psyllium fiber", as used herein, means the seed coat of psyllium seed (either intact or macerated or otherwise comminuted).

Psyllium fiber comes from psyllium seed, from plants of the Plantago genus. Various species such as *Plantago lanceolate*, *P. rugelii*, and *P. major*, are known. Commercial psyllium includes the French (black; *Plantago indica*), Spanish (*P. psyllium*) and Indian (blonde; *P. ovata*). Indian (blonde) psyllium is preferred for use herein.

Intact or macerated seeds can be used in the practice of this invention. However, it is typical to remove the seed coats from the rest of the seed by, for example, slight mechanical pressure, and then to use only the seed coat. In the practice of the present invention it is convenient and desirable to use macerated seed coat in the final composition. The seed coat is therefore preferably removed and sanitized by methods known in the art prior to use in the present composition. Furthermore, the psyllium fiber utilized preferably has high purity, being about 85% to about 100% pure, and more preferably being about 95% to about 100% pure.

While for purposes of the present invention it is possible to have the psyllium fiber dispersed in the palatable food grade fat along with the sennosides, it is preferred that the psyllium comprise one part of the composition (preferably in unit dose form) and the sennosides/fat comprise another part of the composition. Thus, preferred forms for the composition of the present invention include: sandwich-type wafers wherein the sennoside/fat portion is layered between psyllium-containing wafers; coated wafers wherein the sennoside/fat portion coats one surface of a psyllium-containing wafer; and enrobed wafers wherein the sennoside/fat portion encases a psyllium-containing wafer. (For purposes of the present invention, "coated" and "coating" by the sennoside/fat dispersion of psyllium-containing compositions means layering or enrobing or otherwise similarly contacting the dispersion with the psyllium component to prepare such preferred forms and the like according to the present invention.) Preferred for such forms comprising psyllium-containing wafer are extruded psyllium-containing wafers or bars prepared as described in European Patent Application Publication No. 144,644, published Jun. 19, 1985 by G. D. Searle & Co., and baked wafer compositions as described in European Patent Application Publication No. 309,029, published Mar. 29, 1989 by The Procter & Gamble Company (the disclosures of both these publications being incorporated by reference herein in their entirety), and those described in detail hereinafter.

The laxative compositions of the present invention comprise a safe and effective amount of psyllium fiber, typically from about 5% to about 25% psyllium fiber, preferably from about 5% to about 20% psyllium fiber, and more preferably from about 10% to about 15% psyllium fiber, by weight of the laxative composition.

(b) Sennoside

Sennosides are plant-derived compounds that belong to the anthraquinone group of stimulant laxatives. Sennosides are derived from the leaves or pods of various species of the Cassia plant. Commercial sources include the species *Cassia angustifolia* (Tinnevelly senna) and *Cassia acutifolia* (Cassia senna or Alexandria senna). Commercially, sennosides are available as pods, leaves, or concentrates of the leaves and/or pods, and therefore, as used herein, sennoside includes not only the pure or concentrated sennoside compounds having laxative properties but also senna plant materials which have laxative properties. Frequently sold concentrates range from 20%-95% calcium sennosides. The remaining components in the concentrate also originate from the plant, or are formed during extraction. Sennosides supplied from concentrates of senna pods are preferred. Such concentrates have ranges of sennoside content typically from about 20% to about 80%. Obviously, the higher the sennoside level in such concentrates, the less concentrate needed for the laxative compositions. Sennosides are also described in detail in *The Merck Index*, 10th Edition (1983), No. 8298 ("Senna") and No. 8299 ("Sennoside A&B") and in "Proceedings, First International Symposium on Senna", *Pharmacology*, 36, Suppl. 1 (Karger; 1988), incorporated by reference herein in their entirety.

For purposes of the present invention, it is necessary that sennosides be dispersed in whole or in part in the palatable food grade fat having a melting point within the range of from about 30° C. to about 50° C. It is to be noted that when referred to herein as a dispersion of sennosides in the fat material, it is to be understood that this means the sennosides are distributed throughout all or only part of the fat material, and preferably evenly distributed. As noted hereinbefore, it is possible to include some or all of the psyllium fiber also within this fat with the sennoside, but preferred is the use of the sennoside/fat dispersion as a coating on a psyllium-containing phase.

The laxative compositions of the present invention comprise a safe and effective amount of sennosides, typically from about 0.01% to about 5%, and preferably from about 0.1% to about 1% by weight of the laxative composition.

(c) Palatable Food Grade Fat

The compositions of the present invention also comprise a palatable food grade fat having a melting point within the range of from about 30° C. to about 50° C., and preferably within from about 30° C. to about 45° C. Although many fats fall into this category, it has been found that fats commercially available for use in food products which are suitable for inclusion in the laxative compositions of this invention generally include food grade vegetable fats which are substantially solid at room temperature but melt within the prescribed range such as cocoa butter, palm kernel oil, and palm oil; and a number of other hard butters or vegetable oils which have been fractionated, hydrogenated or partially hydrogenated to make such oils solid at room temperature and melt within the prescribed range. Typically, such hardened vegetable oils which are suitable for use in the practice of this invention include hardened coconut oil, cottonseed oil, soybean oil, and the like. Mixtures of aforementioned naturally hard butters and hardened vegetable oils are also suitable for use in the practice of this invention. The preferred food grade fats include cocoa butter and other vegetable fats and oils which, after treatment, have the following general characteristics: a distinct brittle fracture below about 20° C., a fairly sharp, complete melting at within about 35° C. to about 40° C., with an incipient fusion or softening at about 30° C. to about 35° C.

As a practical matter, hardened food grade fats (other than cocoa butter) are commercially available in the form of what is known as "compound coatings" or "confectionary coatings." Compound coatings and/or confectionary coatings are terms of art familiar to those who formulate food products and contain, as essential ingredients, a hardened fat, a sweetener and flavoring material which are therefore preferred optional materials for use in the present invention. Compound coatings and confectionary coatings also contain a number of non-essential optional materials including emulsifiers, food acidulents, salt, and like additives There are a number of confectionary coatings for which particular standards of identity have been established, such as sweet chocolate, milk chocolate, buttermilk chocolate, skim milk chocolate, mixed dairy products, sweet cocoa and vegetable fat coating, and milk chocolate and vegetable fat coating. Such confectionary and compound coatings are suitable and preferred for use in the practice of this invention provided that such materials comprise the necessary level of palatable food grade fat for the present invention compositions. As will be seen hereinafter, additional vegetable fat may be added to commercially available compound coatings during the preparation of the composition of this invention. It should be noted that, in commercially available compound coatings and confectionary coatings containing a mixture of vegetable fats or butters, the individual oils, and/or their concentrations, in such mixture may vary depending on the availability and price of vegetable oils at the time the compound coating is being manufactured.

The laxative compositions of the present invention typically comprise from about 1% to about 50% by weight of palatable food grade fat having a melting point within the range of about 30° C. to about 50° C., preferably from about 1% to about 25%, and most preferably from about 1% to about 10% by weight of the laxative composition.

(d) Optional Components

The present compositions also preferably optionally comprise other dietary fiber, and more preferably insoluble dietary fiber. The term "insoluble dietary fiber", as used herein, means the water insoluble, substantially non-swellable component of fiber material safe for human ingestion which is non-digestible and non-metabolizable by humans.

A wide range of materials containing insoluble dietary fiber may be used in the present invention. Preferred are cereal brans and mixtures thereof, due to their relatively high content of insoluble dietary fiber. Also preferred is that these cereal brans comprise at least about 75% of the insoluble dietary fiber. Cereal brans preferred include those selected from the group consisting of wheat, corn, barley, rye, oats and mixtures thereof. Most preferred are oat or corn. The components of the insoluble dietary fiber from these cereal brans are known to be cellulose, hemicellulose and lignin.

Compositions of the present invention preferably comprise from about 1% to about 20% of an insoluble dietary fiber, and more preferably from about 5% to about 10% insoluble dietary fiber, by weight of the laxative compositions.

For laxative compositions of the present invention wherein the psyllium fiber is present in a baked wafer form, the present laxative compositions further preferably comprise a shortening component. Fats which can be used as the shortening component for such baked psyllium-containing wafer portion of the present compositions can be any of the usual fat stocks employed in preparing liquid, fluid, plastic, or solid shortenings, preferably having a solid content of less than about 25 at room temperature, more preferably having a solid content of less than about 10 at room temperature, and most preferably having a solid content of about 0 at room temperature. Various fats such as cottonseed oil, soybean oil, lard, and other vegetable, animal and marine fats, or mixtures thereof, either unhydrogenated or in various stages of hydrogenation, can be used. Suitable shortening components can also be formulated with non-absorbable, non-digestible fatty acid esters of polyols, in particular sucrose polyesters (disclosed in Jandacek et al. U.S. Pat. No. 4,005,196, issued Jan. 25, 1977, which is incorporated by reference herein in its entirety), and/or other non-nutritive or reduced calorie fat substitute materials suitable for use in the present compositions.

The laxative compositions of the present invention preferably comprise from about 10% to about 20% of the shortening component by weight of the laxative compositions.

The present compositions comprising psyllium in a baked wafer form also preferably comprise a flour component. Any type of flour which is suitable in doughs can be used in the present invention. For example, suitable flours include wheat flour, rye flour, corn flour, cottonseed meal, and sorghum flour. Preferably, wheat flour is used in preparing the cookie compositions for the present invention. This flour can be bleached or unbleached. Furthermore, starches may constitute a portion of the flour component of the present compositions (preferably less than about 5% of the baked composition). Preferred are pregelatinized food starch (e.g., pregelatinized wheat starch; pregelatinized corn starch). Examples of such starches include: Sta-Mist 7415 starch, Sta-Mist 463 starch, and Sta-Mist 454 starch (all sold by A. E. Staley Manufacturing Company; Decatur, Ill.). The baked wafer composition for use in preparing the present laxative compositions preferably comprise from about 1% to about 4%, and more preferably from about 1.5% to about 3%, of pregelatinized food starch by weight of the baked cookie composition.

The compositions of the present invention preferably comprise from about 10% to about 40% flour component by weight of the laxative compositions.

The present compositions also most preferably comprise a sweetening agent. This includes materials such as are described in Moskowitz U.S. Pat. No. 4,766,004, issued Aug. 23, 1988 (incorporated by reference herein in its entirety) which are: water-soluble sweetening agents such as monosaccharides, disaccharides, and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof; water-soluble artificial sweeteners such as the soluble saccharin salts, i.e., sodium or calcium saccharin salts, cyclamate salts, acesulfam-K and the like, and the free acid form of saccharin; or dipeptide based sweeteners such as L-aspartyl-L-phenylalanine methyl ester and materials described in U.S. Pat. No. 3,492,131 and the like. In general, the amount of sweetener is primarily a matter of taste preference and will vary with the sweetener selected and with the ingredients in the composition being prepared. Preferred are non-nutritive artificial sweeteners such as aspartame, acesulfame, saccharin, cyclamate and/or a sugar component such as sucrose, invert sugar syrups, brown sugar, corn syrup solids, fructose, dextrose (glucose), honey, molasses, maple syrup and the like. Particularly preferred sugar components are sucrose, fructose and corn syrup solids.

The compositions of the present invention preferably comprise from about 5% to about 50% of a sweetening agent, and more preferably from about 20% to about 50% of a sweetening agent by weight of the laxative compositions. Also preferred for those compositions wherein the sennoside is dispersed in a confectionery coating containing the required fat and sweetening agent, such coating compositions preferably comprise sweetening agents in amounts of from about 25% to about 75%, more preferably from about 5% to about 60%, by weight of the confectionery coating composition.

The compositions of the present invention also preferably contain only low levels of water, typically in the range of from about 1.5% to about 3.5%. Thus, while a psyllium containing dough for preparing a baked wafer form for the present compositions prior to baking typically contains substantially more water than this, the dough is baked for a time and at a temperature sufficient to reduce the water content in the psyllium-containing compositions to this level.

The water content of such psyllium-containing dough prior to baking is typically in the range of from about 5% to about 15% by weight of the dough. It is to be noted that the weight percentages of the components hereinbefore stated for baked compositions are by weight of the composition following baking. The weight percentages of these components in the dough are therefore proportionally reduced by an amount which depends on the level of water present in the dough. Finally, it is preferred that wafer dough be baked soon after preparation since storage of the dough could adversely effect the efficacy and/or aesthetics of the psyllium in the laxative composition.

Another preferred optional component is one or more emulsifiers. Suitable optional emulsifiers include mono- and diglycerides and fatty acids, sucrose partial fatty acid esters, sorbitan esters of fatty acids, polyoxyethylene sorbitan esters of fatty acids, propylene glycol esters, polyethylene glycol esters, ethoxylated mono- and diglycerides, fumarated esters of monoglycerides or their alkali metal salts, alkanoyl lactylates or their metal salts, lecithins, and the like. Specific dough conditioners include sorbitan monostearate (Span 60), polyoxyethylene sorbitan monostearate (Tween 60), propylene glycol monostearate, glycerol lactopalmitate, sodium stearoyl fumarate, calcium stearoyl-2-lactylate, ethoxylated monoglycerides and lecithin. The amount of emulsifier can be varied to obtain the properties desired.

Another preferred optional component for laxative compositions comprising a baked psyllium-containing forms is one or more leavening agents. Non-yeast leavening agents include a source of carbon dioxide such as sodium bicarbonate or potassium bicarbonate, alone or in combination with a leavening acid such as monocalcium phosphate, dicalcium phosphate, sodium acid pyrophosphate, sodium aluminum sulfate, sodium aluminum phosphate, potassium acid tartrate and the like. The amount of leavening agent used depends on the particular agent employed and the leavening characteristics desired.

Other optional components which may be included are milk products such as whole milk, skim milk, buttermilk, whey, concentrated milk product (condensed or evaporated milk), dried milk products, nonfat milk powder, dry whole milk, modified whole milk and the like, egg products, including egg whites and egg yolks, protein sources (e.g., soy protein), spices, cocoa powder, flavors such as vanilla, salt, color additives, pharmaceutical actives (e.g., analgesics), preservatives, antioxidants and the like. Flavoring agents are preferred optional components and typically comprise from about 0.1% to about 25% by weight of the laxative compositions.

Methods for Making Laxative Compositions

Methods according to the present invention for manufacturing laxative compositions according to the present invention comprise the steps of: (a) heating to melt a palatable food grade fat having a melting point within the range of from about 30° C. to about 50° C.; (b) mixing sennosides with said melted fat at a temperature not above about 75° C., preferably not above about 55° C.; and (c) combining the sennoside/fat-containing mixture with psyllium. Preferred is a process wherein in step (c) the sennoside/fat containing mixture is used to coat a psyllium-containing composition (preferably a baked wafer form as described hereinbefore).

Methods of Treating Constipation

The present invention also relates to a method for treating constipation in humans or lower animals in need of such treatment. This method comprises orally administering to a human or lower animal in need of such treatment a safe and effective amount of a composition of the present invention. Ingestion of from about 1 gram to about 50 grams per day (typically in amounts of from about 1 gram to about 5 grams per dose) of the psyllium fiber and about 5 mg to about 250 mg per day (typically in amounts of from about 5 mg to about 50 mg per dose) of sennosides from compositions according to the present invention is appropriate in most circumstances to produce laxation. However, this can vary with the size and condition of the patient, and such matters will, of course, be apparent to the attending physician. The term "safe and effective amount", as used herein, means an amount of psyllium fiber and sennoside, when used according to the compositions and methods of the present invention, high enough to significantly positively affect the constipation to be treated but low enough to avoid serious side effects (at a reasonable benefit/risk ratio), within the scope of sound medical judgment.

The following example further describes and demonstrates an embodiment within the scope of the present invention. The example is given solely for the purpose of illustration and is not to be construed as a limitation of the present invention as many variations thereof are possible without departing from the spirit and scope.

EXAMPLE

A sennoside/fat-coated psyllium-containing wafer composition according to the present invention in the form of a sennoside-containing chocolate flavored coating on a baked psyllium-containing wafer is prepared as follows having the following composition.

| Components | Weight % |
|---|---|
| (a) Psyllium wafer | 83.0% |

| Wafer Components | Weight % (by weight of dough before baking) |
|---|---|
| Fructose | 6.91 |
| Sucrose | 12.33 |
| Molasses | 0.50 |
| Water | 3.51 |
| Psyllium | 12.30 |
| Oat Fiber | 6.51 |
| Corn Oil | 15.03 |
| Lecithin | 1.00 |
| Starch | 2.00 |
| Water | 3.31 |
| Soda | 0.20 |
| Cinnamon | 0.90 |
| Nutmeg | 0.25 |
| Vanilla Flavor | 0.20 |
| Butter Flavor | 0.20 |
| Ascorbic Acid | 0.15 |
| Flour | 20.39 |
| Sucrose | 5.29 |
| Oats | 9.02 |

| (b) Sennoside/fat-containing coating | 17.0% |
|---|---|

| Coating Components | Weight % (by weight of coating) |
|---|---|
| Chocolate-flavored non-tempering coating[1] | 98.8% |
| Senna concentrate[2] | 1.2% |

[1] CF-1037 non-tempering confectionary coating supplied by Ambrosia Chocolate Company, Milwaukee, Wisconsin [melting point approximately 102° F. (39° C.); containing: sugar (49-53%); hydrogenated cotton seed and soybean oils (35-37%); dry whey (4-6%); cocoa (3-5%); chocolate liquor (3-5%); distilled monoglyceride/sorbitan monostearate (less than 2%); salt (0.04-0.06%); and pure vanilla (0.04-0.06%)]

[2] 71.3% Sennosides A & B supplied by Leiras Medicia. Turku, Finland.

The psyllium wafer is prepared from a dough formed by mixing a warmed mixture of psyllium, lecithin, and oil, and oat fiber, and fructose, sucrose, molasses, and water, followed by mixing in water, cinnamon, nutmeg, vanilla, butter flavor, ascorbic acid, and starch, followed by mixing in flour and soda, and then mixing in the remaining sucrose and finally the oats. This dough is moulded into rectangles (approximately 6.35 cm×4.06 cm×0.76 cm) and baked in a 3 zone oven for 7-8 minutes at 325°-395° F. (162°-202° C.) and then cooled (final water content approximately 2.3%).

The sennoside/fat-containing coating component is prepared by melting the chocolate at 112°-115° F. (44°-46° C.) with agitation and mixing with the sennosides, being careful not to let temperatures exceed 115° F. (46° C.). An enrober is then used to coat the baked psyllium wafers prepared as described hereinbefore with this sennoside/fat-containing coating in an amount to provide 4.0 grams of coating per each 19.5 g wafer.

Use of this process ensures that the composition prepared contains psyllium and sennosides which are effective, well tolerated and consumer acceptable for treating constipation in humans or lower animals. One wafer ingested by a patient in need of relief from constipation produces laxation.

What is claimed is:

1. Laxative compositions comprising:
  (a) from about 5% to about 25% of psyllium fiber;
  (b) from about 0.01% to about 5% of sennoside;
  (c) from about 1% to about 50% of palatable food grade fat having a melting point within the range of from about 30° C. to about 45° C., said food grade fat being selected from the group consisting of cocoa butter, palm kernel oil, palm oil, coconut oil, cottonseed oil, soybean oil, and mixtures thereof; and
  (d) from about 5% to about 40% of sweetening agent, and wherein further at least a part of said sennoside is dispersed in a confectionary base comprising said palatable food grade fat which coats a psyllium-containing composition in unit dose form.

2. Laxative compositions according to claim 1 wherein said psyllium composition in unit dose form is a baked wafer.

3. Laxative compositions according to claim 2 wherein said palatable food grade fat comprises cocoa butter.

* * * * *